(12) United States Patent
Verma et al.

(10) Patent No.: US 12,027,269 B2
(45) Date of Patent: Jul. 2, 2024

(54) INTELLIGENT SYSTEM AND METHODS FOR AUTOMATICALLY RECOMMENDING PATIENT-CUSTOMIZED INSTRUCTIONS

(71) Applicant: CERNER INNOVATION, INC., Kansas City, KS (US)

(72) Inventors: Megha Verma, Bengaluru (IN); Imran Shaikh, Bengaluru (IN); Andrew Arun Kumar Boppuri, Bengaluru (IN); Prashant Pagi, Bengaluru (IN)

(73) Assignee: Cerner Innovation, Inc., Kansas City, MO (US)

( * ) Notice: Subject to any disclaimer, the term of this patent is extended or adjusted under 35 U.S.C. 154(b) by 502 days.

(21) Appl. No.: 17/103,404

(22) Filed: Nov. 24, 2020

(65) Prior Publication Data
US 2022/0165415 A1  May 26, 2022

(51) Int. Cl.
*G16H 50/20* (2018.01)
*G06Q 50/20* (2012.01)
(Continued)

(52) U.S. Cl.
CPC ........... *G16H 50/20* (2018.01); *G06Q 50/205* (2013.01); *G16H 10/60* (2018.01); *G16H 15/00* (2018.01); *G16H 40/20* (2018.01); *G16H 50/70* (2018.01)

(58) Field of Classification Search
CPC .. G16H 50/20–26; G16H 50/70; G16H 40/20; G16H 15/00; G16H 10/60; G06Q 50/205
See application file for complete search history.

(56) References Cited

U.S. PATENT DOCUMENTS

| 10,339,272 B2 * | 7/2019 | Draghi | G16H 40/63 |
| 2010/0082369 A1 * | 4/2010 | Prenelus | G16H 40/67 |
| | | | 705/3 |

(Continued)

FOREIGN PATENT DOCUMENTS

| WO | WO-02067775 A1 * | 9/2002 | ........... A61B 5/7435 |
| WO | WO-2015191562 A1 * | 12/2015 | ......... G06F 19/3418 |
| WO | WO-2017089387 A1 * | 6/2017 | ............. G06F 19/00 |

OTHER PUBLICATIONS

Saunders et al., Bring on the Machines: Could Machine Learning Improve the Quality of Patient Education Materials? A Systematic Search and Rapid Review, 2 JCO Clinical Cancer Informatics 1-16 (Dec. 2018) (Year: 2018).*

*Primary Examiner* — Jordan L Jackson
(74) *Attorney, Agent, or Firm* — Invoke

(57) ABSTRACT

Methods, systems, and computer-readable media are disclosed herein for automatically identifying and selecting, based on machine learning model(s), one or more patient educations instructions as suggested smart recommendations for a particular patient, based on parameter matching and filtering with other patient parameters. The parameters of a current patient can be automatically matched to parameters that are associated with other patients, on a one-to-one parameter basis or based on specific combinations parameters. Based on the presence of one or more shared parameters between a current patient and other patients as well as the strength of the parameter match, one or more instructions that were provided to the other patients can be recommended for the current patient automatically. Instruction(s) selected for the current patient can then be stored in association with the parameters of the current patient and used to evaluate and make recommendations for subsequent patients.

20 Claims, 8 Drawing Sheets

(51) Int. Cl.
*G16H 10/60* (2018.01)
*G16H 15/00* (2018.01)
*G16H 40/20* (2018.01)
*G16H 50/70* (2018.01)

(56) References Cited

U.S. PATENT DOCUMENTS

2013/0262140 A1* 10/2013 Friedlander ............ G16H 40/20
　　　　　　　　　　　　　　　　　　　　　　　705/3
2016/0063212 A1*  3/2016 Monier ................. G16H 10/60
　　　　　　　　　　　　　　　　　　　　　　　705/3
2016/0063214 A1*  3/2016 Blue ................. G06F 16/24578
　　　　　　　　　　　　　　　　　　　　　　　705/3
2017/0262604 A1*  9/2017 Francois ............... G16H 10/60
2018/0137247 A1*  5/2018 Bore ..................... G16H 80/00
2018/0277252 A1*  9/2018 Drenkard ............... G16H 50/20
2018/0330061 A1* 11/2018 Amiel ................... G16H 20/10
2020/0342335 A1* 10/2020 Burke ................... G16H 20/00
2020/0402630 A1* 12/2020 Sudharsan .............. G06N 5/04
2020/0411162 A1* 12/2020 Lien ...................... G16H 50/70

* cited by examiner

INTELLIGENT SYSTEM AND METHODS FOR AUTOMATICALLY RECOMMENDING PATIENT-CUSTOMIZED INSTRUCTIONS

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description.

One aspect of the present disclosure relates to a non-transitory computer-readable storage medium having instructions embodied thereon, the instructions being executable by one or more processors to perform a method for smart patient education recommendations using artificial intelligent and machine learning techniques. In an aspect, a first plurality of parameters are identified for a first patient. Then, a pattern of the first plurality of parameters of the first patient is determined to, at least, partially match a pattern of a second plurality of parameters of a second patient using one or more machine learning models wherein the first patient and the second patient are different individuals, in some aspects. In response to determining that the pattern of the first plurality of parameters at least partially matches the pattern of the second plurality of parameters, one or more patient education instructions that are associated with the second patient are identified, in an aspect. The one or more patient education instructions are communicated as recommendations for the first patient, in such aspects.

In another aspect, one or more non-transitory computer-readable storage media having instructions embodied thereon are provided wherein the instructions are executable by one or more processors to perform a method. In one such aspect, an indication to provide one or more recommendations is received. A first plurality of parameters is identified for a first patient. In some aspects, a pattern of the first plurality of parameters of the first patient are determined to, at least, partially match a pattern of a second plurality of parameters of a plurality of patients based on one or more machine learning models. In response to determining that the pattern of the first plurality of parameters at least partially matches of the second plurality of parameters of the plurality of patients, a score is calculated for each of the plurality of patients that at least partially match the first plurality of parameters of the first patient, in such aspects. One or more patient education instructions that are associated with the plurality of patients that at least partially match the first plurality of parameters of the first patient are retrieved, in aspects. In one aspect, the one or more patient education instructions are communicated as the one or more recommendations. The one or more patient education instructions are communicated for display, ranked by the score that corresponds to each of the plurality of patients that at least partially match the first plurality of parameters of the first patient, in some aspects.

In one aspect, the present disclosure relates to a system. The system includes a memory and one or more processors coupled to the memory, in aspects. Further, the system includes a parameter matching module, in some aspects. The parameter matching module can receive an indication to provide one or more recommendations and can identify a first plurality of parameters for a first patient, in some aspects. Additionally, the parameter matching module can, in some aspects, determine that a pattern of the first plurality of parameters of the first patient, at least, partially matches a pattern of a second plurality of parameters of a plurality of patients by using one or more machine learning models. The system can include a match scoring module, in various aspects. The match scoring module can, in response to the determination that the pattern of the first plurality of parameters at least partially matches of the second plurality of parameters of the plurality of patients, calculate a score for each of the plurality of patients. The system includes, in some aspects, a recommendation module. In such aspects, the recommendation module retrieves one or more patient education instructions that are associated with each of the plurality of patients that at least partially match the first plurality of parameters of the first patient. The recommendation module communicates, in one aspect, the one or more patient education instructions as the one or more recommendations, wherein the one or more patient education instructions are communicated for display ranked by the score that corresponds to each of the plurality of patients that at least partially match the first plurality of parameters of the first patient.

BRIEF DESCRIPTION OF THE DRAWINGS

Illustrative aspects of the present invention are described in detail below with reference to the attached drawing figures, and wherein:

Figure 4:
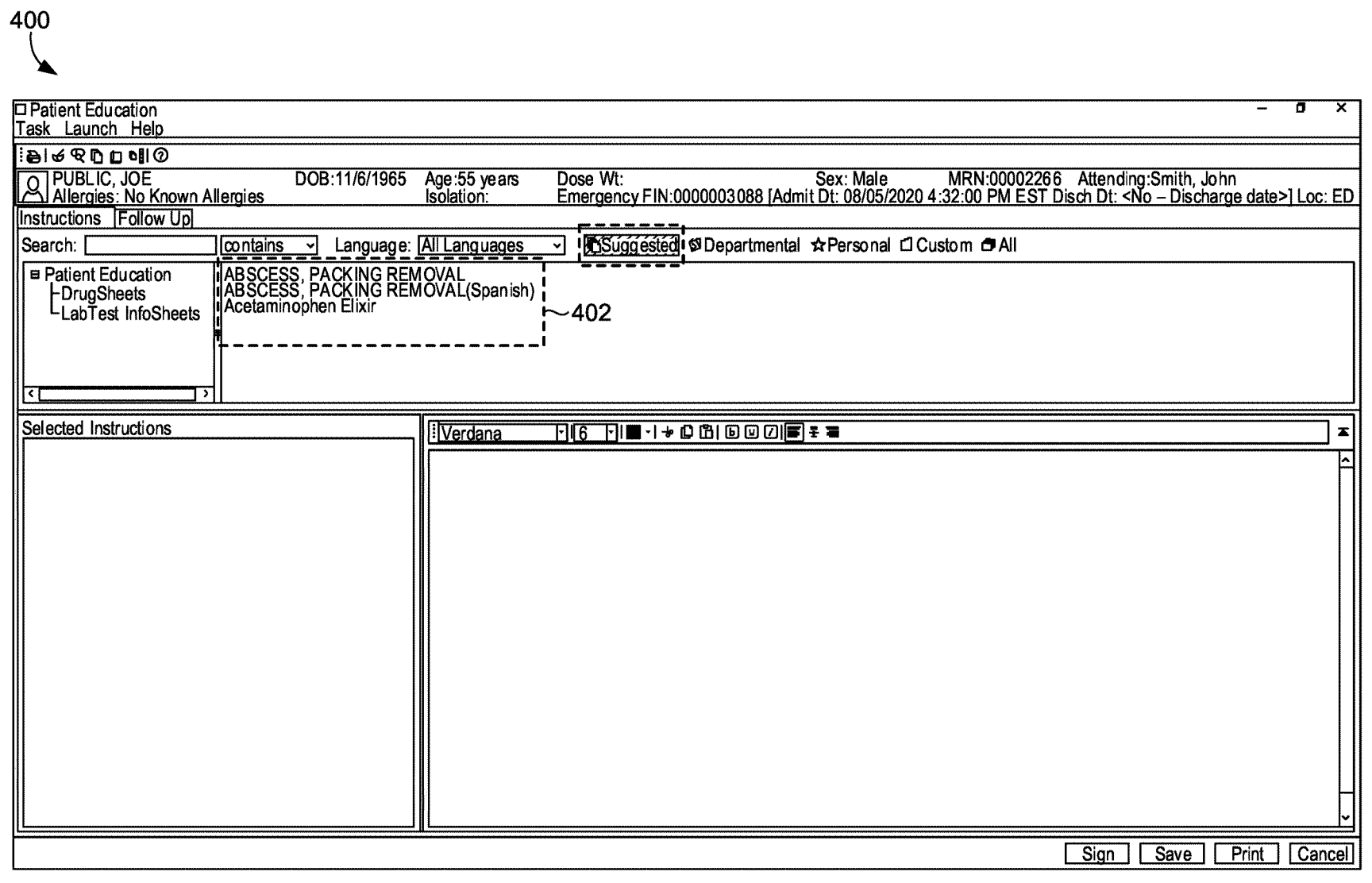
Figure 5:
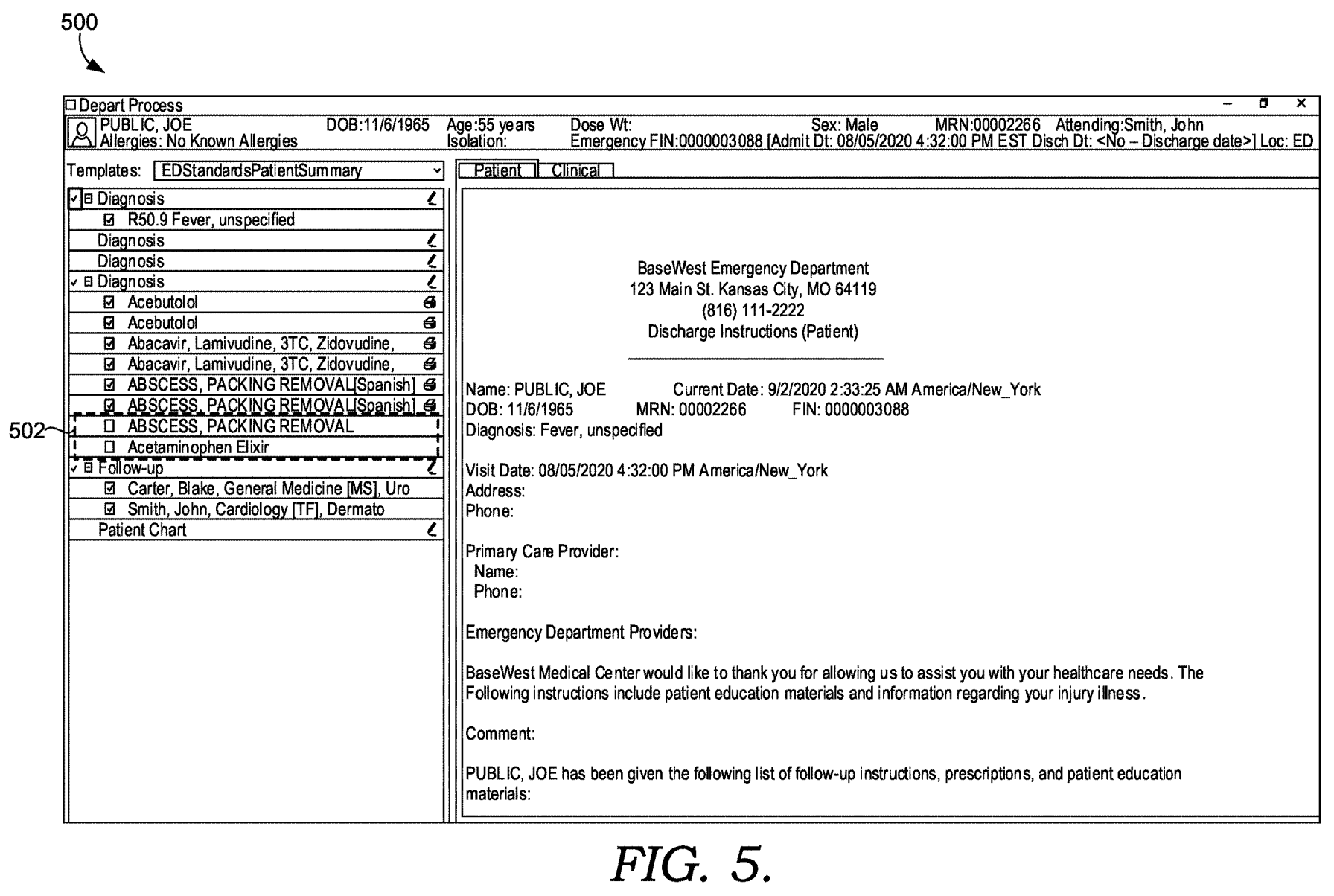
Figure 7:
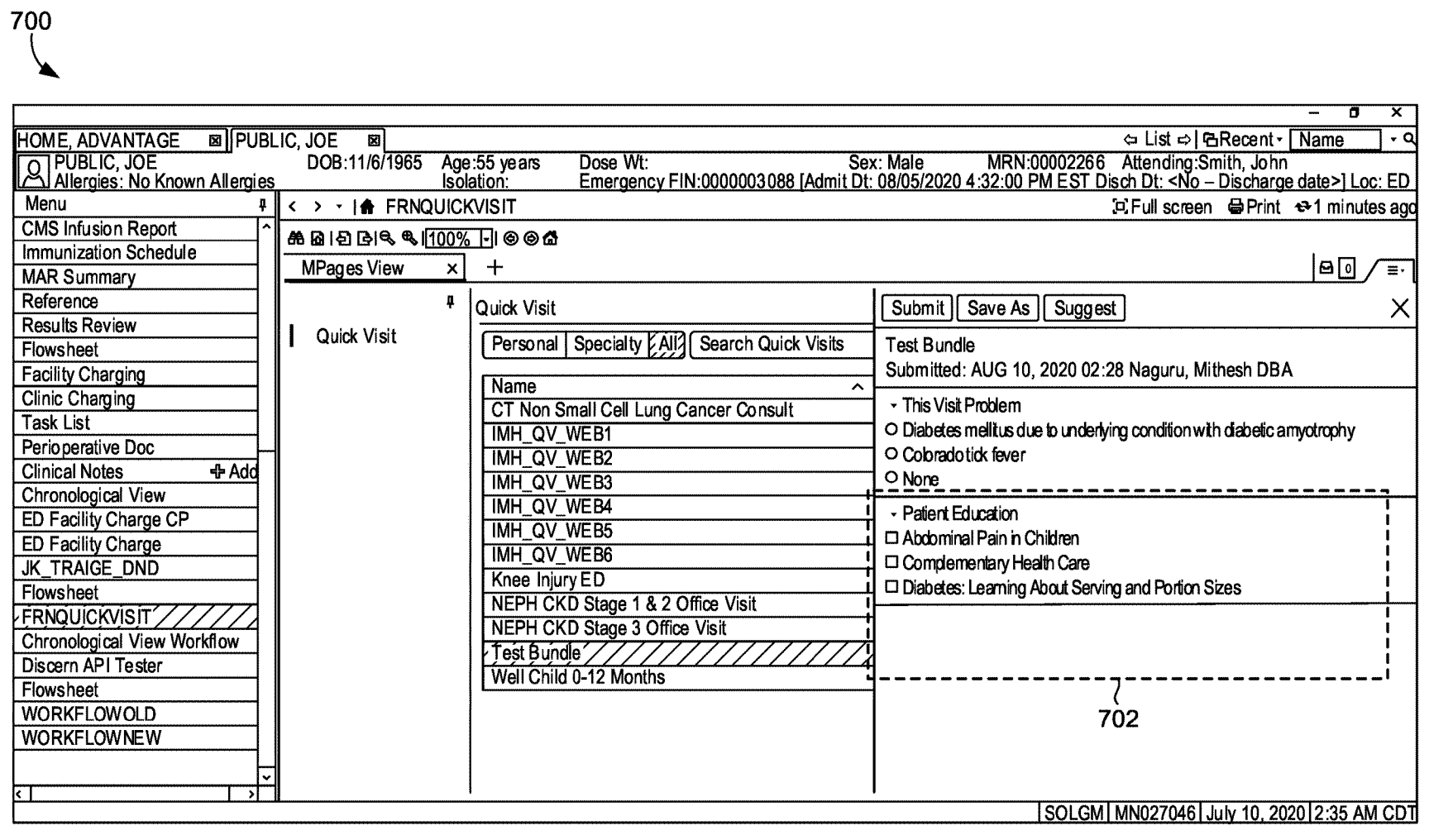

FIGS. 4 through 7 depicts example graphical user interfaces that automatically display smart patient-education recommendations for user selection, in accordance with aspects discussed herein.

DETAILED DESCRIPTION

Figure 1:
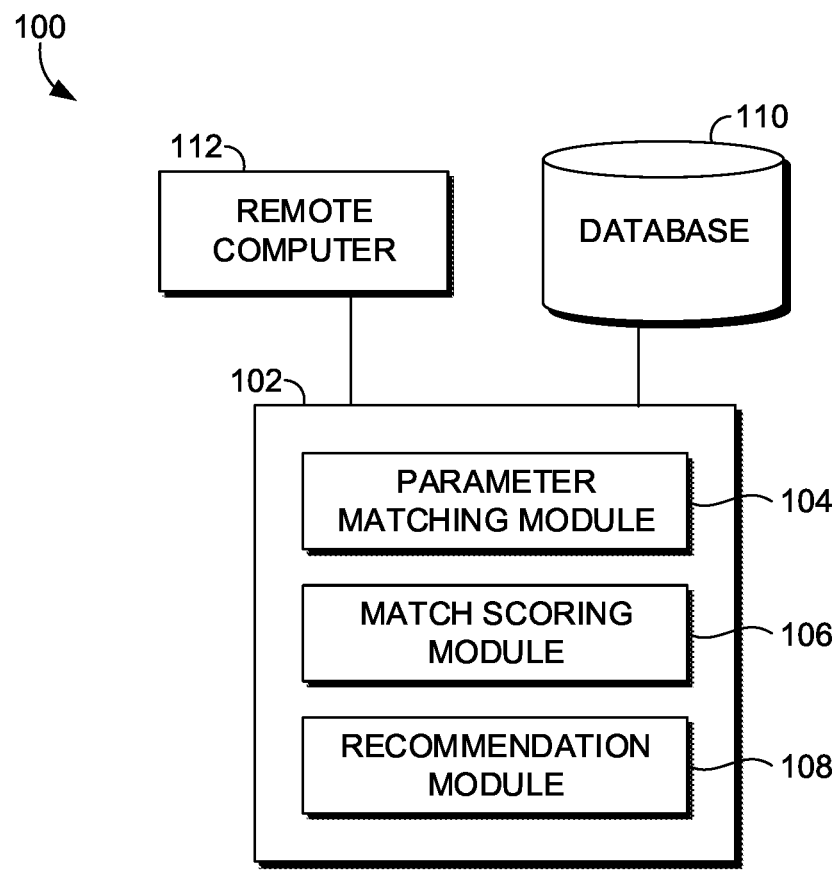
FIG. 1 illustrates a system architecture, in accordance with aspects discussed herein.

The subject matter of the present invention is being described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Terms should not be interpreted as implying any particular order among or between various steps herein disclosed unless and except when the order of individual steps is explicitly described. As such, although the terms "step" and/or "block" may be used herein to connote different elements of system and/or methods, the terms should not be interpreted as implying any particular order and/or dependencies among or between various components and/or steps herein disclosed unless and except when the order of individual steps is explicitly described. The present disclosure will now be described more fully herein with reference to the accompanying drawings, which may not be drawn to scale and which are not to be construed as limiting. Indeed, the present invention can be embodied in many different forms and should not be construed as limited to the embodiments set forth herein.

A system, methods, and computer media described hereinafter provide a computerized tool or service that automatically identifies, selects, and recommends, in a patient customized manner, education instructions. When a patient's clinical encounter is to be electronically documented in a computerized healthcare system, for example, information is gathered from the patient, from one or more clinicians, and/or from a corresponding EMR of the patient (if available), such as a chief complaint, a reason for visit, and one or more presenting problems. For example, when the patient is being admitted to an inpatient service, is being checked-in for an outpatient clinical encounter, or an intake is performed in an acute setting (e.g., urgent care), the patient may provide information using a form or via an interview at the time of the clinical encounter or even prior using a mobile application, for example. This information can be used and/or combined with information obtained from the patient's EMR and/or a clinician in order to, by way of an automated computer service or tool described hereinafter, identify and provide "smart" recommendations for patient education instructions. As used herein, the term "smart" refers to the use of artificial intelligence and machine learning to intelligently make recommendations that suggest specific patient education instructions to be provided to a patient, where this "smart recommendations" are specific to the particular parameters of a patient being analyzed by the artificial intelligence and machine learning, and thus, the smart recommendations are "customized" to the parameter pattern of the patient. Via the automated computer service or tool, a plurality of parameters that are specific to the current patient can be automatically identified within or extracted from the information, and used to identify a plurality of other patients that share one or more of the same or similar parameters, as documented previously for other clinical encounters, for example. The parameters' presence or absence captured for other previously documented patients may be stored and accessed via data store, for example, in order to filter out patients that do not share common parameters with the current patient and to retain those patients that do share common parameters with the current patient. By way to the automated computer service or tool, it can be predicted whether one or more patient education instructions that were previously documented as being used for the patients that share one or more of the same or similar parameters as the current patient should be communicated to a clinician for the current patient, as recommended patient education instructions. The patient education instructions that are predicted to be relevant to the current patient are then communicated to a user, such as a clinician, for use by and dissemination to the current patient.

For example, for a current patient presenting with a parameter of "suggested knee replacement," the computerized service or tool can search a data store of tens of thousands of patients using the parameter to identify 9,956 other individual patients having the same parameter of a "suggested knee replacement." One or more of the patient education instructions that were previously documented as being used for the 9,956 patients are predicted to be relevant to the current patient and are automatically communicated to a clinician for the current patient, as recommended patient education instructions. (The patient education instructions that were previously documented as being used for the 9,956 patients may be stored in association with the patients in the data store.). Additionally, for the same current patient who presents with a parameter of "hip pain" as a chief complaint in addition to "suggested knee replacement," 3,454 patients (which may or may not overlap in some portion with the 9,956 patients) having the same chief complaint parameter of "hip pain" can be searched and located in the data store. One or more of the patient education instructions that were previously documented as being used for the 3,454 patients are predicted to be relevant to the current patient and are automatically communicated to a clinician for the current patient, as recommended patient education instructions. Thus, parameter matching may be performed on a one-to-one parameter basis, to identify multiple sets of patients that have at least one parameter in common with the current patient.

In addition to the one-to-one parameter matching discussed above, parameter matching may be performed for parameter combinations (e.g., patterns) within the same analysis of the current patient. In the example, for the current patient presenting with a parameter pattern of "suggested knee replacement" and chief complaint parameter of "hip pain," 274 total patients from the 9,956 patient cohort and the 3,454 patient cohort may share the same parameter pattern of both "suggested knee replacement" and "hip pain." One or more of the patient education instructions that were previously documented as being used for the 274 patients are predicted by the computerized service or tool to be relevant to the current patient based on the matching parameters, and are automatically communicated to a clinician for the current patient, as recommended patient education instructions.

As such, any quantity, type, and combination of parameters may be identified for a current patient and used to search for and filter through patients and associated parameter(s) that are stored in a data store. Examples of parameter types include age, gender, race, language, a chief complaint, a reason for a patient encounter, a presenting problem, a preliminary diagnosis, a final diagnosis, a clinician specialty, a medical history, a surgical history, a medication history, and an education instruction. Accordingly, a current patient's unique parameter "pattern" (e.g., the unique and specific combination of their parameters and the values for each parameter) can be partially or completely matched to one or more patients with corresponding parameter values and patterns. As the quantity of common parameters shared by the current patient and another patient increases, the computerized service or tool increases the predicted relevancy of the prior patient's education instructions relative to the current patient for which recommendations are to be made by the service or tool.

Accordingly, improving the relevancy of patient education instructions for specific patients improves patient outcomes. The aspects provided for herein improve patient health outcomes by reducing the total number of inpatient days per year experienced by patients (e.g., ≥80% reduction), reducing clinical complications of patients, and reducing hospitalization and treatment costs incurred by healthcare facilities and by the patients (e.g., ≥70% decrease). The benefits provided by accurately targeting patient education materials to specific individual patients, especially when aggregated across an entire healthcare system, cannot be underestimated in terms of both population health and healthcare costs. Further still, the aspects herein improve healthcare entity compliance with governmental and legal requirements or guidelines that require the distribution of patient education instructions.

Beginning with FIG. 1, a system environment 100 is depicted. The system environment 100 shown in FIG. 1 includes a system 102, a database 110, and a remote computer 112. The system 102 includes a memory and one or more processors coupled to the memory (not shown) for executing computer-executable instructions stored on computer-readable storage media, such as memory. In some aspects, the system 102 comprises a utility or application, whether run locally or web-based, that performs backend (e.g., user-invisible) operations and functions to automatically determine patient-specific or "smart" recommendations for patient education instructions.

The system 102 includes a parameter matching module 104. In some aspects, the parameter matching module 104 receives an indication to provide one or more recommendations. The recommendations may be requested for a particular "first" patient, in aspects. The parameter matching module 104 may identify a first plurality of parameters for that first patient, in response to or based on the indication received that requests recommendations, for example. The parameter matching module 104 determines whether a pattern of the first plurality of parameters identified for the first patient at least partially matches a pattern of a second plurality of parameters of a plurality of patients. As mentioned above, for example, the parameter matching module 104 may search for and determine 9,956 other individual patients have the same parameter of a "suggested knee replacement" as the first patient, based on a search of a data store for a plurality of patients having corresponding parameters. Additionally or alternatively, the parameter module 104 may search for and determine that 3,454 patients (which may or may not overlap in some portion with the 9,956 patients) have the same chief complaint parameter of "hip pain," based on a search of the data store, for example, as discussed above.

Generally, the parameter matching module 104 references a plurality of patients, each having and being associated with a unique parameter pattern of their own, all being stored in a data store, whether local or remote. The parameter matching module 104 matches each of the parameters in the first plurality of parameters of the first patient to the unique parameter patterns of the other patients, for example, in attempting to locating one or more individual patients that have a pattern which is a "best" match (e.g., a highest quantity or a threshold quantity of matching parameters) to the first patient's parameter pattern. In some aspects, the parameter matching module 104 may locate all patients that have a parameter pattern that includes at least one matching parameter to the first patient's parameter pattern. In further aspects, the parameter matching module 104 may locate all patients that have a parameter pattern that includes at least two matching parameters to the first patient's parameter pattern. In some aspects, the parameter matching module 104 may locate all patients that have a parameter pattern that include, at least or exactly, all the plurality of a parameters identified for the first patient's parameter pattern.

The parameter matching module 104 may select only a portion of the located or identified matching patients to server as candidate sources for subsequent patient education instruction recommendations, in some aspects. For example, a selected portion of the matching patients might correspond to a top half (or percentage such as 75%, 25%, 10%, 5%) of all the patients that were determined to have at least one matching parameter to the first patient's parameter pattern, in some aspects. In various example, a "top" half or a "top" quartile refers to, respectively, a 50% or 25% portion of the patients having the greatest quantity of matching parameters relative to the whole. As such, a selected portion corresponds to the patients having a greatest quantity of matching parameters to the first patient's parameter pattern, for example. The selected portion of matching patients may be used subsequently to identify patient education instructions that are stored in the data store, in association with corresponding patients for which the patient education instructions have been documented as being applicable, used, or applied in other clinical encounters, for example.

Continuing, the system 102 includes a match scoring module 106. In some aspects, the match scoring module 106 can calculate a score for each of the plurality of patients that at least partially match the first plurality of parameters of the first patient. For example, the scores for each patient that matches at least one parameter can be automatically calculated in response to determining that the pattern of the first plurality of parameters at least partially matches of the second plurality of parameters of the plurality of patients. The match scoring module 106 may calculate a score for only the selected portion of matching patients, for example, as selected by the parameter matching module 104, in a further aspect. For example, only a half, a quarter, or other portion (e.g., ration or percentage) of the patients that meet a minimum quantity of matching parameters may be scored, either individually, or as cohorts.

The system 102 includes a recommendation module 108, in various aspects. In some aspects, the recommendation module 108 retrieves one or more patient education instructions that are associated with the plurality of patients that at least partially match the first plurality of parameters of the first patient. For example, patient education instructions that were provided to one or more of the plurality of patients that at least partially match the first plurality of parameters of the first patient can be used as recommendations to the first patient. In another example, patient education instructions that were provided to a selected cohort of the plurality of patients that at least partially match the first plurality of parameters of the first patient can be used as recommendations to the first patient. The patient education instructions may be stored in association with each of the patients in the data store, in some aspects, where the instructions were documents as having been previously provided to those patients in prior patient encounters. The recommendation module 108, in various aspects, can communicate the one or more patient education instructions as the one or more recommendations to be provided, automatically, for the first patient. The one or more patient education instructions are communicated for display, for example, ranked by the score that corresponds to each of the plurality of patients (e.g., individually or as cohorts) that at least partially match the first plurality of parameters of the first patient, in some aspects.

Regarding FIG. 1, it should be understood that the placement of various components is an abstraction such that one or more of the various components may be located or may operate anywhere within the system environment 100, and as such, the depicted arrangement is only an example. Accordingly, other components and arrangements may be used additionally or instead of that which is depicted, such that one or more depicted components may be omitted, for example. Further, the components shown may be implemented as discrete components, distributed components, or in conjunction with other components, and in any suitable combination and physical or virtual location. The functions described herein as being performed by one or more components, entities, and/or devices may be carried out by hardware, firmware, and/or software, in embodiments, such that the functions are not limited unless explicitly described as such.

It should also be understood that the system environment 100 shown in FIG. 1 is only one example of a suitable environment, and this example has been simplified for ease of discussion. Accordingly, other components not shown may also be included within the environment, and one or more of the shown components may be omitted, in various embodiments. Each of the components of FIG. 1 may be implemented using any type or number of computing devices, in embodiments. The components may communicate with each other directly or, for example, indirectly via a network, including one or more of a telecommunication network, a local area network (LANs), a wide area network (WANs), and/or a peer-to-peer-network. Such networking environments may include campus-wide or enterprise-wide computer networks, intranets, and the Internet. It should be understood that any number of components shown in FIG. 1 may be employed within the system environment 100 within the scope of the present invention. Each may be implemented via a single device or multiple devices cooperating in a distributed environment.

Figure 2:
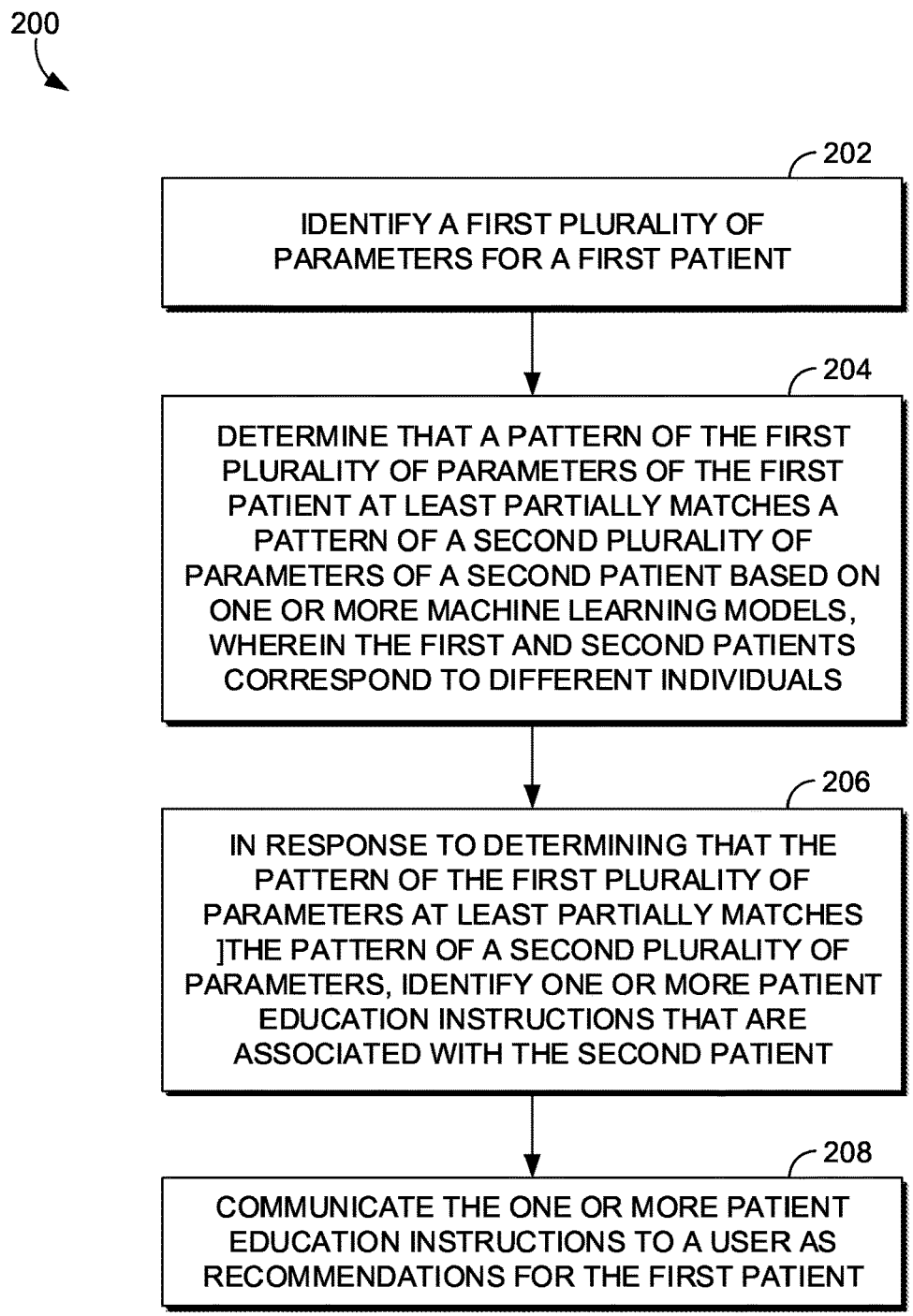
FIG. 2 depicts a flowchart of a method, in accordance with aspects discussed herein.
Figure 3:
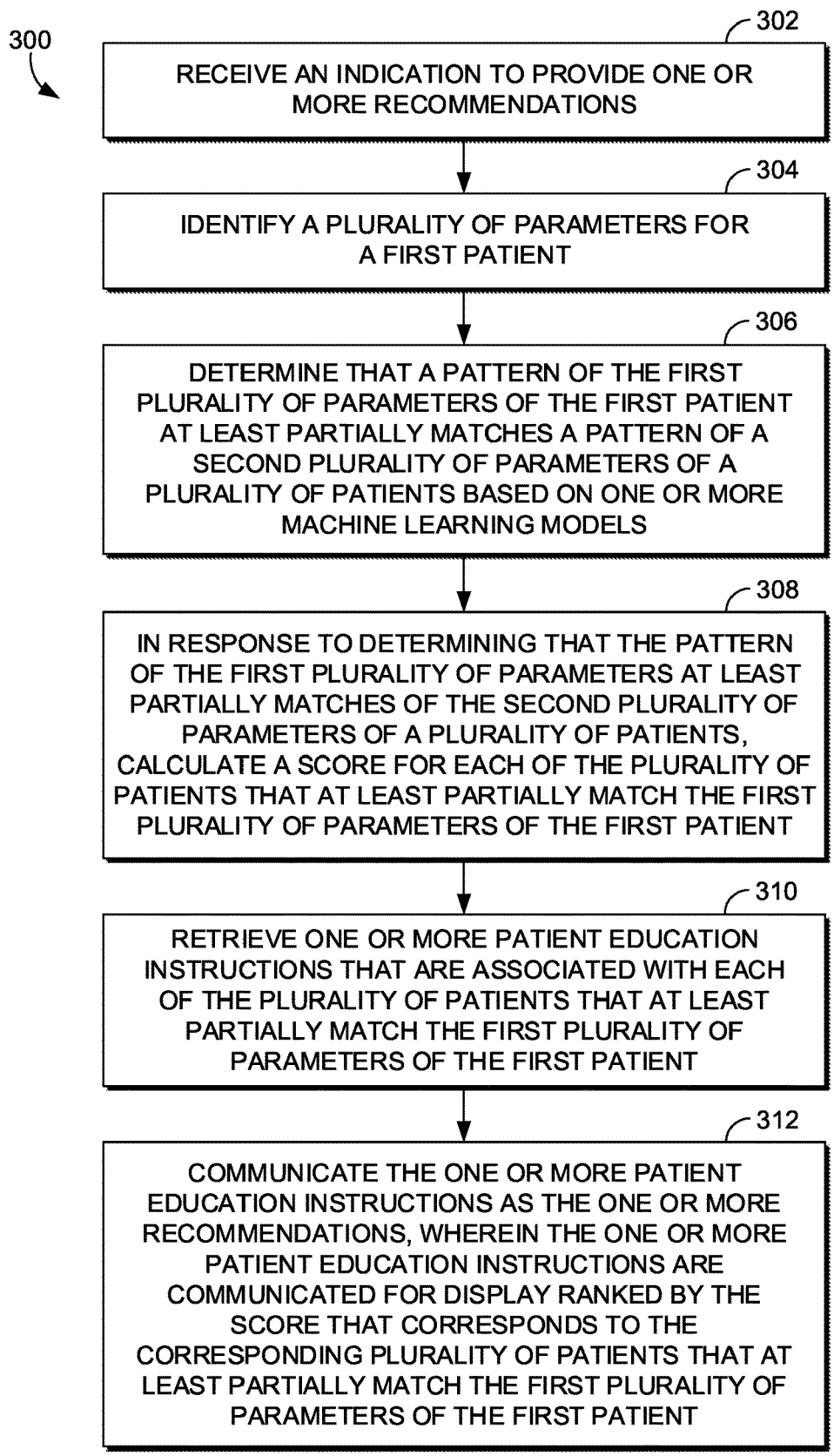
FIG. 3 depicts a flowchart of another method, in accordance with aspects discussed herein.
Figure 6:
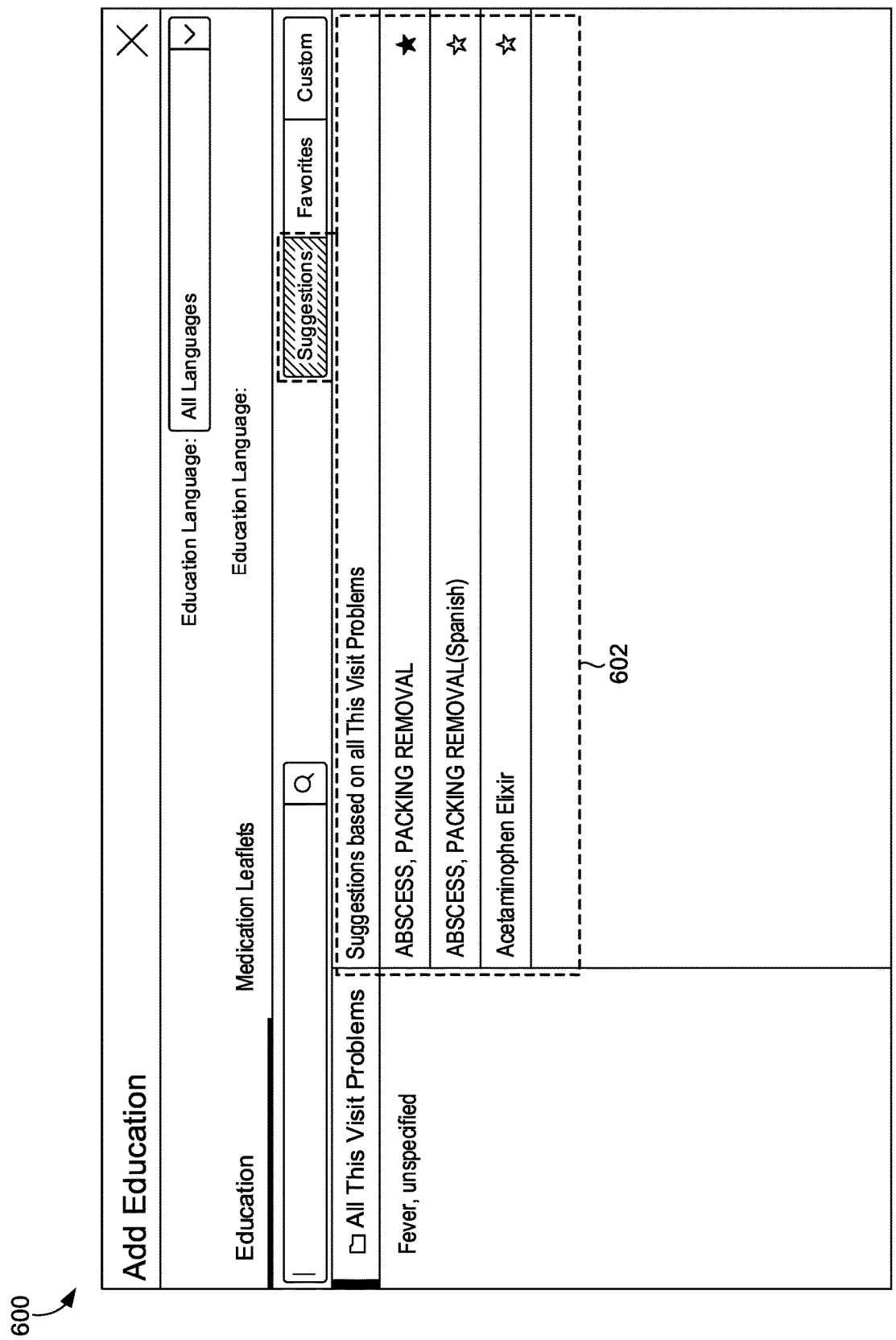

Turning to FIGS. 2 and 3, methods are discussed that can be performed via one or more of the system, components, and/or component interactions previously described in FIG. 1. As such, the methods are discussed briefly for brevity, though it will be understood that the previous discussion and details described therein can be applicable to aspect of the methods of FIGS. 2 and 3. Additionally or alternatively, it will be understood that the methods discussed herein can be implemented or performed via the execution of computer-readable instructions stored on computer readable media, by one or more processors. As such, the methods 200 and 300 may be computer-implemented, in some embodiments. In one embodiment, one or more non-transitory computer-readable storage medium having computer-readable program code portions embodied therein are used to implement the methods 200 and 300. For example, the computer-readable program code portions may include one or more executable portions configured to perform the methods 200 and 300, in an embodiment. The computer-readable program code may correspond to a utility or application, wherein the application performs the methods 200 and 300, in some embodiments. As further discussed below, the methods 200 and 300 may be performed using the system 102 and components shown in FIG. 1.

FIG. 2 depicts a flowchart of a method for automatically identifying and selecting patient education that will be suggested recommendations for a particular patient, based on parameter matching and filtering, in accordance with some aspects of the present invention. At block 202, a first plurality of parameters is identified for a first patient. The first plurality of a parameters is specific to the first patient. Examples of parameter types include age, gender, race, language, a chief complaint, a reason for a patient encounter, a presenting problem, a preliminary diagnosis, a final diagnosis, a clinician specialty, medical history, surgical history, an education instruction, and treatment (medication) history. The parameters may be automatically identified by parsing one or more electronic forms, digital sound or voice data, digital images, or other data that capture patient information and/or clinician-provided input before, during, or after a patient encounter, in aspects.

At block 204, a pattern of the first plurality of parameters of the first patient is determined to, at least, partially match a pattern of a second plurality of parameters of a second patient based on one or more machine learning models, wherein the first patient and the second patient are different individuals. Examples of machine learning model types may include a recommendation model, a clustering model, and/or a classification model. As used herein "pattern" refers to one or more parameters and/or combination of parameters identified for that one individual patient. For example, a first patient may have a pattern of: Caucasian female, age 45 years (e.g., with age range of 40-45 years), positive diabetes mellitus II diagnosis, a current prescription for metformin 500 mg once a day, a medical history of neuropathy in the feet, and a medical history of migraines. In some aspects, a parameter may include a negative test result (e.g., negative influenza test result), the absence of a diagnosis (e.g., no cancer diagnosis), and/or items absent from the medical history (e.g. no medical history of heart disease, no medical history of receiving a vaccine for hepatitis B). This unique pattern of the first patient's plurality of parameters is used to search for, identify, and compare to other patterns of other patients. As such, a second patient can be identified as having a unique pattern that at least partially matches the first patient based on the second patient's parameter pattern including, for example, a Caucasian female, positive diabetes mellitus II diagnosis, a current prescription for metformin 500 mg once a day, and a medical history of migraines. In this example, the second patient has no history of medical history of neuropathy in the feet, so the second patient's parameter pattern only partially matches the first patient's parameter pattern in this example. Further, the second patient may have one or more additional parameters that are not shared by and/or do not match to the first patient's parameter pattern, and these one or more additional parameters are not considered for the comparison, in some aspects.

In another example, a first patient may have a pattern of a patient-provided chief complaint (e.g., painful walking on right foot), a clinician-input reason for visit (e.g., follow-up on acute right foot pain), and one or more presenting problems (i.e., a list of active medical diagnosis and/or high priority conditions that may be related to or completely independent of the complaint and reason for visit). This unique pattern of the first plurality of parameters of the first patient, for example, can be partially or completely matched to a unique pattern of a second plurality of parameters of one or more additional patients (e.g., a second patient), wherein the second plurality of parameters have the same or similar patient-provided chief complaint, clinician-input reason for visit, and one or more presenting problems. The type, quantity, specificity, and detail of the first patient's parameter pattern may vary based on the circumstances of the clinical encounter with the first patient, for example, as the availability of information may vary. For example, the different types and the specificity of various parameters identified may vary based on whether the first patient has been treated within a specific medical system previously, whether the current patient encounter is inpatient, outpatient, emergent, or non-emergent, and/or whether the intake of the first patient captures large or small amounts of information.

Accordingly, the unique pattern of the first patient's plurality of parameters is used to automatically search for and identify other parameters and/or parameter patterns that are unique to other patients, in aspect, via one or more processors and without additional user input. In one aspect, determining that the pattern of the first plurality of parameters at least partially matches the pattern of a second plurality of parameters includes determining that a portion of the first plurality of parameters match one or more of the second plurality of parameters, in various aspects. In one such aspect, the portion of the first plurality of parameters are identical to at least a portion of the second plurality of parameters. In another aspect, determining that the pattern of the first plurality of parameters at least partially matches the pattern of the second plurality of parameters of the second patient includes determining that each of the first plurality of parameters matches one or more of the second plurality of parameters. In yet another aspect, determining that the pattern of the first plurality of parameters of the first patient at least partially matches the pattern of the second plurality of parameters of the second patient includes determining that a majority of the first plurality of parameters match the second plurality of parameters, wherein the majority of the first plurality of parameters are identical to at least a portion of the second plurality of parameters. When the majority of first plurality of parameters have been matched, additional parameters in the first plurality of parameters may continue to be used to search and match other parameters in the data store of other patient in an effort to find a better or strongest match to one or more other patients' parameter patterns (e.g., the greatest quantity matching parameters). For example, six of ten parameters (e.g., parameter pattern of parameters 1, 2, 3, 4, 5, 6 are matched) of a first patient's parameter pattern may be matched with a plurality of other patient's parameter patterns, but the remaining four parameters can also be matched to determine whether a greater majority match can be made with one or more other patients' parameter patterns (e.g., parameter pattern of parameters 1, 2, 3, 4, 5, 8, 9, and 10 are matched).

In aspects, determining that the pattern of the first plurality of parameters of the first patient at least partially matches the pattern of the second plurality of parameters of the second patient includes determining when a threshold quantity or threshold percentage of the first plurality of parameters match the second plurality of parameters. The threshold quantity or threshold percentage of the first plurality of parameters may be identical to at least a portion of the second plurality of parameters, for example. In a further aspect, determining that the pattern of the first plurality of parameters of the first patient at least partially matches the pattern of the second plurality of parameters of the second patient includes determining that all of the first plurality of parameters match the second plurality of parameters of second patient. For example, all ten parameters of a first patient's unique parameter pattern may be matched to the unique parameters of a second patient. In another example, all three parameters of a first patient's unique parameter pattern may be matched to the unique parameters of a second patient. As the quantity of available parameters of the first patient increases, searching and locating matching parameter patterns of other patients can be filtered for greater and greater specificity, in some aspects. Although a "second" patient is discussed herein, it should be understood that the first patient can be matched to a plurality of other patients, and the second patient is merely one example.

In response to determining that the pattern of the first plurality of parameters at least partially matches the pattern of the second plurality of parameters of the second patient, one or more patient education instructions that are associated with the second patient are identified, as shown at block 206. For example, a plurality of patient education instructions there were previously selected by a clinician for the second patient can be retrieved from a database. In some aspects, the parameter matching module 104 of FIG. 1 may determine which parameters of a first patient match one or more parameter patterns of other patients. In further aspects, the match scoring module 106 of FIG. 1 may score the matches based on the quantity and/or type or parameters that match one another, and the recommendation module 108 of FIG. 1 may retrieve, based on the strength of the match, patient education instructions that are associated with the other second patient as potential recommendations to be made for the first patient and provided to a clinician. Where the first patient's parameter pattern is matched to multiple other patients, patient education instructions that are associated with one or more of these other patients can be identified and provided as potential recommendations to be made for the first patient.

At block 208, the one or more patient education instructions are communicated as recommendations for the first patient. Accordingly, other patients having the same or similar parameter patterns as the first patient may act as sources to provide highly relevant, patient-education instructions as suggested recommendations for the first patient, independent of whether or not the same or similar clinical workflows are common with the first patient. As such, increasingly relevant patient education instructions recommendations can be made that overcome the limitations imposed by a computerized system's pre-defined clinical workflow or diagnostic workflow. Therefore, in some aspects, the one or more patient education instructions that are associated with the second patient are identified as corresponding to at least one of the second plurality of parameters that at least partially match the first plurality of parameters. The one or more patient education instructions that are associated with the second patient are identified as corresponding to all of the second plurality of parameters that match the first plurality of parameters, in one aspect. In some aspects, the recommendation module 108 of FIG. 1 can determine and communicate the one or more patient education instructions as recommendations for the first patient.

The patient education instructions can be communicated for presentation, for example, via a graphical user interface. FIGS. 4 through 7 provide example graphical user interfaces that communicate the one or more smart patient recommendations to a user, such as a clinician. For example, the graphical user interface 400 of FIG. 4 includes a plurality of patient education recommendations 402, for the specific individual JOE PUBLIC, shown as "ABSCESS, PACKING REMOVAL", "ABSCESS, PACKING REMOVAL (Spanish)", "Acetaminophen Elixir." In another example, the graphical user interface 500 of FIG. 5 includes a plurality of patient education recommendations 502 shown as "ABSCESS, PACKING REMOVAL" and "Acetaminophen Elixir." In FIG. 6, the graphical user interface 600 also includes a plurality of patient education recommendations 602 shown as "ABSCESS, PACKING REMOVAL", "ABSCESS, PACKING REMOVAL (Spanish)", "Acetaminophen Elixir." And in FIG. 7, the graphical user interface 700 includes a plurality of patient education recommendations 702 "Abdominal Pain in Children", "Complementary Healthcare", and "Diabetes: Learning About Serving and Portion Sizes" for the patient JOE PUBLIC. It will be understood that the graphical user interfaces of FIGS. 4 through 7 are merely examples, and other methods of communicating patient education instructions are contemplated and are within the scope of this disclosure.

Continuing to FIG. 3, a flowchart of another method 300 is depicted for automatically identifying and selecting highly relevant, patient-education instructions as suggested recommendations for the first patient, based on parameter matching and filtering, in accordance with some aspects of the present invention. For brevity, some steps, features, and details of the method 300 may be discussed at a high level, as these steps, features, and details have already been discussed at length with regard to FIGS. 1 and 2, for example. Beginning at block 302, an indication to provide one or more recommendations is received, for example, for a first patient. At block 304, a first plurality of parameters for the first patient are identified. The parameters of the first patient may be identified by the parameter matching module 104 of FIG. 1, for example. The first plurality of parameters may be identified in response to receipt of the indication to provide one or more recommendations, in some aspects. In other aspects, the first plurality of parameters may be identified prior to receipt of the indication for recommendation(s), for example, based on the first patient being admitted for care, whether inpatient or outpatient. At block 306, a pattern of the first plurality of parameters of the first patient is determined to, at least, partially match a pattern of a second plurality of parameters of a plurality of patients based on one or more machine learning models, as previously described. The parameter matching module 104 of FIG. 1 may, in some aspects, determine that the pattern of the first plurality of parameters of the first patient at least partially matches a pattern of a second plurality of parameters of a plurality of patients. In response to determining that the pattern of the first plurality of parameters at least partially matches of the second plurality of parameters of the plurality of patients, a score is calculated for each of the plurality of patients that at least partially match the first plurality of parameters of the first patient, as shown at block 308. In one such aspects, the match scoring module 106 of FIG. 1 may calculate a score for each of the plurality of patients (or for each cohort) that at least partially match the first plurality of parameters of the first patient, in response to the determination that the pattern of the first plurality of parameters at least partially matches of the second plurality of parameters.

At block 310, one or more patient education instructions that are associated with the plurality of patients that at least partially match the first plurality of parameters of the first patient are retrieved. The recommendation module 108 of FIG. 1 may retrieve the patient education instructions, in some aspects. The one or more patient education instructions retrieved correspond to at least one of the partially-matching second plurality of parameters, in various aspects, as determined using one or more machine learning models, for example. In some aspects, the patient education instructions that are retrieved are specific to one or more of the second plurality of parameters of the plurality of patients determined to at least partially match the first plurality of parameters, and the second plurality of parameters may include one or more of a chief complaint, a reason for a patient encounter, a presenting problem, a preliminary diagnosis, and/or a final diagnosis, for example. Additionally or alternatively, the second plurality of parameters may include two or more of a chief complaint, a reason for a patient encounter, a presenting problem, a preliminary diagnosis, or a final diagnosis.

At block 312, the one or more patient education instructions are communicated as the one or more recommendations, wherein the one or more patient education instructions are communicated for display ranked by the score that corresponds to each of the plurality of patients that at least partially match the first plurality of parameters of the first patient. The ranking of the one or more patient education instructions may further be determined by the score, as based on one or more machine learning models. The recommendation module 108 of FIG. 1 may communicate the patient education instructions, in some aspects. The score represents a strength of the at least partially matching of the pattern of the first plurality of parameters of the first patient to the second plurality of parameters of the plurality of patients. Thus, in such examples, the plurality of patients that at least partially match the first plurality of parameters of the first patient are ranked based on the score calculated for each of the plurality of patients. For example, the patient education instructions that are associated with a patient having the highest score (relative to the scores of other at least partially matching patients) may be communicated and presented at the top of a list, with the patient education instructions in descending score order.

In further aspects, a selection of at least one of the one or more patient education instructions that were communicated may be received, for example, via the graphical user interfaces of FIGS. 4 through 7. In response to receiving the selection, the at least one of the one or more patient education instructions that was selected may become associated with the first plurality of parameters and with the first patient, for example. This associated may further be made using one or more machine learning models, in some examples. In aspects, the at least one selected patient education instruction can be stored in association with the first plurality of parameters and in association with the first patient in the data store. The first plurality of parameters of the first patient may then be used to subsequently determine pattern matching for a subsequent patient, and further, the at least one of the one or more patient education instructions can be subsequently communicated as a recommendation for the subsequent patient. Accordingly, user selections of patient recommended education instructions are used to support future patient education recommendations based on parameter pattern matching. For example, each time a clinician selects a specific patient education instruction to be utilized for the first patient, the computerized service or tool recognizes that the selected instruction(s) are to be associated with the first patient's parameter pattern. Thus, each patient education instruction that is selected (e.g., selected and signed by the clinician) is used by for making recommendations to subsequently assessed patients, and the knowledge base in the data store grows over time.

Additionally or alternatively, a selection of a user-provided patient education instruction may be received (e.g., an education instruction that was not one of the automatically recommended instructions). In response to receiving the selection, the user-provided patient education instruction that was selected can become associated with the first plurality of parameters and with the first patient, for example. This association may be created, in some examples, by using the one or more machine learning models. In one example, the user-provided patient education instruction can be stored in association with the first plurality of parameters and in association with the first patient. The first plurality of parameters of the first patient can then be used to subsequently determine pattern matching for a subsequent patient and the user-provided patient education instruction may be subsequently communicated as a recommendation for one or more subsequently assessed patients. Accordingly, user-provided recommendations can also be used to support future patient education recommendations, and can grow the knowledge base in the data store.

Figure 8:
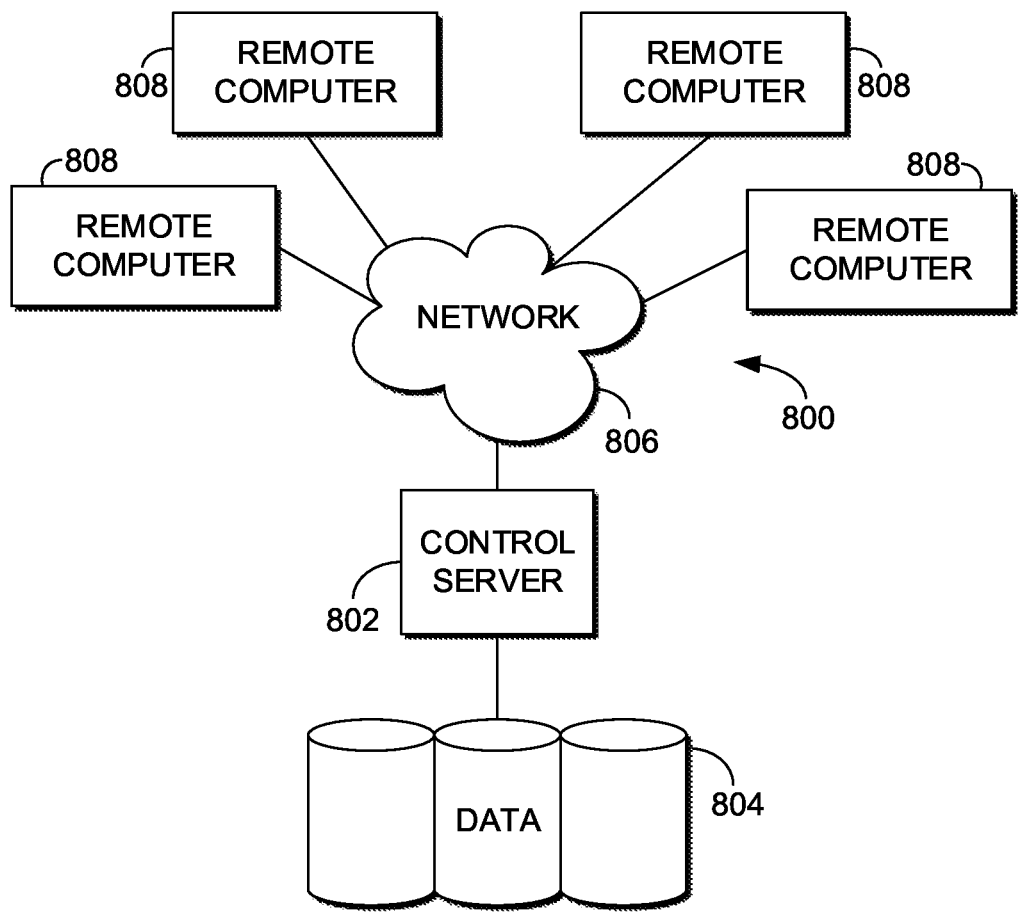
FIG. 8 depicts a computing environment, in accordance with aspects discussed herein.

Turning now to FIG. 8, a computing environment 800 that is suitable for use in implementing aspects of the present invention is depicted. The computing environment 800 is merely an example of one suitable computing environment and is not intended to suggest any limitation as to the scope of use or functionality of the invention. Neither should the computing environment 800 be interpreted as having any dependency or requirement relating to any single component or combination of components illustrated therein. Generally, in aspects, the computing environment 800 is a medical-information computing-system environment. However, this is just one example and the computing environment 800 can be operational with other types, other kinds, or other-purpose computing system environments or configurations. Examples of computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

In aspects, the computing environment 800 can be described in the general context of computer instructions, such as program modules, applications, and/or extensions, being read and executed by a computing device. Examples of computer instructions can include routines, programs, objects, components, and/or data structures that perform particular tasks or implement particular abstract data types. The aspects discussed herein can be practiced in centralized and/or distributed computing environments, i.e., where computer tasks are performed utilizing remote processing devices that are linked through a communications network, whether hardwired, wireless, or a combination thereof. In a distributed configuration, computer instructions might be stored or located in association with one or more local and/or remote computer storage media (e.g., memory storage devices). Accordingly, different portions of computer instructions for implementing the computer tool in the computing environment 800 may be executed and run on different devices, whether local, remote, stationary, and/or mobile.

With continued reference to FIG. 8, the computing environment 800 comprises a computing device 802, shown in the example form of a server. Although illustrated as one component in FIG. 8, the present invention can utilize a plurality of local servers and/or remote servers in the computing environment 800. The computing device 802 can include components such as a processing unit, internal system memory, and a suitable system bus for coupling to various components, including electronic storage, memory, and the like, such as a data store, a database, and/or a database cluster. Example components of the computing device 802 include a processing unit, internal system memory, and a suitable system bus for coupling various components, including a data store 804, with the computing device 802. An example system bus might be any of several types of bus structures, including a memory bus or memory controller, a peripheral bus, and a local bus, using any of a variety of bus architectures. Examples of bus architectures include Industry Standard Architecture (ISA) bus, Micro Channel Architecture (MCA) bus, Enhanced ISA (EISA) bus, Video Electronics Standards Association (VESA®) local bus, and Peripheral Component Interconnect (PCI) bus, also known as Mezzanine bus.

The computing device 802 includes or has access to a variety of non-transitory computer-readable media. Computer-readable media can be any available media that is locally and/or remotely accessible by the computing device 802, and includes volatile, nonvolatile, removable, and non-removable media. By way of example, and not limitation, computer-readable media can comprise computer storage media and communication media. Computer storage media includes volatile, nonvolatile, removable, and non-removable media, as implemented in any method or technology for storage of information, such as computer-readable instructions, data structures, program modules, or other data.

The computing device 802 can include or can have access to computer-readable media. Computer-readable media can be any available media that can be accessed by computing device 802, and includes volatile and nonvolatile media, as well as removable and non-removable media. By way of example, and not limitation, computer-readable media can include computer storage media and communication media.

Computer storage media can include, without limitation, volatile and nonvolatile media, as well as removable and non-removable media, implemented in any method or technology for storage of information, such as computer-readable instructions, data structures, program modules, or other data. In this regard, computer storage media can include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which can be accessed by the computing device 802. Computer storage media does not comprise signals per se.

Communication media typically embodies computer-readable instructions, data structures, program modules, or other data in a modulated data signal, such as a carrier wave or other transport mechanism, and can include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also can be included within the scope of computer-readable media.

The computing device 802 might operate in a network 806 using logical connections to one or more remote computers 808. In some aspects, the one or more remote computers 808 can be located at a variety of locations, such as medical facilities, research environments, and/or clinical laboratories (e.g., molecular diagnostic laboratories), as well as hospitals, other inpatient settings (e.g., surgical centers), veterinary environments, ambulatory settings, medical billing offices, financial offices, hospital administration settings, home healthcare environments, and/or clinicians' offices). As used herein, "clinicians," "medical professionals," or "healthcare providers" can include: physicians; specialists such as surgeons, radiologists, cardiologists, and oncologists; emergency medical technicians; physicians' assistants; nurse practitioners; health coaches; nurses; nurses' aides; pharmacists; dieticians; microbiologists; laboratory experts; laboratory technologists; genetic counselors; researchers; veterinarians; students; and the like.

In aspects, the computing device 802 uses logical connections to communicate with one or more remote computers 808 within the computing environment 800. In aspects where the network 806 includes a wireless network, the computing device 802 can employ a modem to establish communications with the Internet, the computing device 802 can connect to the Internet using Wi-Fi or wireless access points, or the server can use a wireless network adapter to access the Internet. The computing device 802 engages in two-way communication with any or all of the components and devices illustrated in FIG. 8, using the network 806. Accordingly, the computing device 802 can send data to and receive data from the remote computers 808 over the network 806.

The network 806 is a computer network that can include local area networks (LANs) and/or wide area networks (WANs), in some aspects. The network 806 can include wireless and/or physical (e.g., hardwired) connections. Examples of networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. When the network 806 includes a WAN-type configuration, the computing device 802 might comprise a modem or other means for establishing communications over the WAN, such as the Internet, in such aspects. As such, the network 806, can provide the components and devices access to the Internet and web-based applications.

The network 806 can include an entity-wide network, campus-wide network, an office-wide network, an enterprise-wide networks, and the Internet. In the network 806, applications, extensions, program modules or portions thereof might be stored in association with the computing device 802, the data store 804, and any of the one or more remote computers 808. For example, various application programs can reside on the memory associated with any one or more of the remote computers 808. In the computing environment 800, which is illustrated as being a distributed configuration of the network 806, the components and devices can communicate with one another and can be linked to each other using a network 806. It will be appreciated by those of ordinary skill in the art that the network connections shown are exemplary and other means of establishing a communications link between the computers (e.g. computing device 802 and remote computers 808) might be utilized.

In operation, an organization might enter commands and information into the computing device 802 or convey the commands and information, for example, directly in peer-to-peer or near-field communication, or through the network 806 using telecommunications or Wi-Fi, to the computing device 802 via one or more of the remote computers 808 through input devices, such as a keyboard, a pointing device (e.g., a mouse), a trackball, as stylus, or a touch pad. Other input devices comprise microphones, satellite dishes, scanners, or the like. Commands and information might also be sent directly from a remote healthcare device to the computing device 802. In addition to a screen, monitor, or touchscreen component, the computing device 802 and/or remote computers 808 might comprise other peripheral output devices, such as speakers and printers.

The computing environment 800 includes one or more remote computers 808, which may be accessed by the computing device 802 over the network 806 or directly using peer-to-peer connections or mesh networking, in various aspects. The remote computers 808 might be servers, routers, network personal computers, peer devices, network nodes, computing devices, personal digital assistants, personal mobile devices, medical devices, patient monitoring equipment, or the like, and might comprise some or all of the elements described above in relation to the computing device 802. The one or more remote computers 808 can include multiple computing devices, in various aspects. In aspects where the network 806 is distributed in configuration, the one or more remote computers 808 can be located at one or more different geographic locations. In an aspect where the one or more remote computers 808 are a plurality of computing devices, each of the plurality of computing devices can be located across various locations such as buildings in a campus, medical and research facilities at a medical complex, offices or "branches" of a banking/credit entity, or can be mobile devices that are wearable or carried by personnel, or attached to vehicles or trackable items in a warehouse, for example. In some aspects, the remote computers 808 are physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. The remote computers 808 might also be physically located in nontraditional healthcare environments so that the entire healthcare community might be capable of integration on the network 806. In other aspects, the remote computers 808 can be physically located in a non-medical setting, such as a packing and shipping facility or deployed within a fleet of delivery or courier vehicles.

Continuing, the computing environment 800 includes a data store 804. Although shown as a single component, the data store 804 can be implemented using multiple data stores that are communicatively coupled to one another, independent of the geographic or physical location of a memory device. The data store 804 can, for example, store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. The data store 804 can, for example, also store data in the form of electronic records, such as electronic medical records of patients, patient-specific documents and historical records, transaction records, billing records, task and workflow records, chronological event records, and the like. Generally, the data store 804 includes physical memory that is configured to store information encoded in data. For example, the data store 804 can provide storage for computer-readable instructions, computer-executable instructions, data structures, data arrays, computer programs, applications, and other data that supports the functions and actions to be undertaken using the computing environment 800 and components shown in the example of FIG. 8.

As shown in the example of FIG. 8, when the computing environment 800 operates with distributed components that are communicatively coupled via the network 806, computer instructions, applications, extensions, and/or program modules can be located in local and/or remote computer storage media (e.g., memory storage devices). Aspects of the present invention can be described in the context of computer-executable instructions, such as program modules, being executed by a computing device. Program modules can include, but are not limited to, routines, programs, objects, components, and data structures that perform particular tasks or implement particular abstract data types. In aspects, the computing device 802 can access, retrieve, communicate, receive, and update information stored in the data store 804, including program modules. Accordingly, the computing device 802 can execute, using a processor, computer instructions stored in the data store 804 in order to perform aspects described herein.

Although internal components of the devices in FIG. 8, such as the computing device 802, are not illustrated, those of ordinary skill in the art will appreciate that internal components and their interconnection are present in the devices of FIG. 8. Accordingly, additional details concerning the internal construction device are not further disclosed herein. Although many other internal components of the computing device 802 and the remote computers 808 are not shown, such components and their interconnection are known. Accordingly, additional details concerning the internal construction of the computing device 802 and the remote computers 808 are not further disclosed herein.

Additionally, it will be understood by those of ordinary skill in the art that the computing environment 800 is just one example of a suitable computing environment and is not intended to limit the scope of use or functionality of the present invention. Similarly, the computing environment 800 should not be interpreted as imputing any dependency and/or any requirements with regard to each component and combination(s) of components illustrated in FIG. 8. It will be appreciated by those having ordinary skill in the art that the connections illustrated in FIG. 8 are also examples as other methods, hardware, software, and devices for establishing a communications link between the components, devices, systems, and entities, as shown in FIG. 8, can be utilized in implementation of the present invention. Although the connections are depicted using one or more solid lines, it will be understood by those having ordinary skill in the art that the example connections of FIG. 8 can be hardwired or wireless, and can use intermediary components that have been omitted or not included in FIG. 8 for simplicity's sake. As such, the absence of components from FIG. 8 should be not be interpreted as limiting the present invention to exclude additional components and combination(s) of components. Moreover, though devices and components are represented in FIG. 8 as singular devices and components, it will be appreciated that some aspects can include a plurality of the devices and components such that FIG. 8 should not be considered as limiting the number of a device or component.

Regarding FIGS. 1 through 8, it will be understood by those of ordinary skill in the art that the environment(s), system(s), and/or methods(s) depicted are not intended to limit the scope of use or functionality of the present embodiments. Similarly, the environment(s), system(s), and/or methods(s) should not be interpreted as imputing any dependency and/or any requirements with regard to each component, each step, and combination(s) of components or step(s) illustrated therein. It will be appreciated by those having ordinary skill in the art that the connections illustrated the figures are contemplated to potentially include methods, hardware, software, and/or other devices for establishing a communications link between the components, devices, systems, and/or entities, as may be utilized in implementation of the present embodiments. As such, the absence of component(s) and/or steps(s) from the figures should be not be interpreted as limiting the present embodiments to exclude additional component(s) and/or combination(s) of components. Moreover, though devices and components in the figures may be represented as singular devices and/or components, it will be appreciated that some embodiments can include a plurality of devices and/or components such that the figures should not be considered as limiting the number of a devices and/or components.

It is noted that embodiments of the present invention described herein with reference to block diagrams and flowchart illustrations. However, it should be understood that each block of the block diagrams and/or flowchart illustrations can be implemented in the form of a computer program product, an entirely hardware embodiment, a combination of hardware and computer program products, and/or apparatus, systems, computing devices/entities, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code can be performed sequentially such that one instruction is retrieved, loaded, and executed at a time. In some embodiments, retrieval, loading, and/or execution can be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

Additionally, as should be appreciated, various embodiments of the present disclosure described herein can also be implemented as methods, apparatus, systems, computing devices/entities, computing entities, and/or the like. As such, embodiments of the present disclosure can take the form of an apparatus, system, computing device, computing entity, and/or the like executing instructions stored on a computer-readable storage medium to perform certain steps or operations. However, embodiments of the present disclosure can also take the form of an entirely hardware embodiment performing certain steps or operations.

Many different arrangements of the various components depicted, as well as components not shown, are possible without departing from the scope of the claims below. Embodiments of our technology have been described with the intent to be illustrative rather than restrictive. Alternative embodiments will become apparent readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. A method for providing smart patient education recommendations via artificial intelligence and machine learning, the method comprising:

generating a knowledge base for training one or more machine learning models, at least one of the one or more machine learning models comprising a clustering model, the knowledge base comprising parameters of prior patients and user selections of education instructions for the prior patients, the parameters including age, gender, language, race, a chief complaint, a reason for a patient encounter, a presenting problem, a preliminary diagnosis, a final diagnosis, a medical history, a clinician specialty, a surgical history, an education instruction, or a medication history;

generating the one or more machine learning models comprising the clustering model from the knowledge base;

identifying a first plurality of parameters for a first patient, the first plurality of parameters includes two or more of age, gender, language, race, a chief complaint, a reason for a patient encounter, a presenting problem, a preliminary diagnosis, a final diagnosis, a medical history, a clinician specialty, a surgical history, an education instruction, or a medication history;

automatically determining, without user input, that a pattern of the first plurality of parameters of the first patient at least partially matches a pattern of a second plurality of parameters of a second patient of the prior patients based on the one or more machine learning models, wherein the first patient and the second patient are different individuals, wherein determining that the pattern of the first plurality of parameters at least partially matches the pattern of the second plurality of parameters comprises:

applying the one or more machine learning models to the parameters of the first patient;

in response to determining that the pattern of the first plurality of parameters at least partially matches the pattern of the second plurality of parameters, automatically identifying, without user input, one or more patient education instructions that are associated with the second patient;

communicating, to a clinician, the one or more patient education instructions as recommendations for the first patient; and responsive to determining that the clinician selected a particular patient education instruction, from the one or more patient education instructions, for the first patient, updating the knowledge base for retraining the one or more machine learning models based on the first plurality of parameters of the first patient and the particular patient education instruction.

2. The method of claim 1, wherein determining that the pattern of the first plurality of parameters of the first patient at least partially matches the pattern of the second plurality of parameters of the second patient based on one or more machine learning models comprises:

determining that a portion of the first plurality of parameters match one or more of the second plurality of parameters, wherein the portion of the first plurality of parameters is identical to at least a portion of the second plurality of parameters.

3. The method of claim 1, wherein determining that the pattern of the first plurality of parameters of the first patient at least partially matches the pattern of the second plurality of parameters of the second patient based on one or more machine learning models comprises:

determining that each of the first plurality of parameters matches one or more of the second plurality of parameters.

4. The method of claim 1, wherein determining that the pattern of the first plurality of parameters of the first patient at least partially matches the pattern of the second plurality of parameters of the second patient based on one or more machine learning models comprises:

determining that a majority of the first plurality of parameters match the second plurality of parameters, wherein the majority of the first plurality of parameters are identical to at least a portion of the second plurality of parameters.

5. The method of claim 1, wherein determining that the pattern of the first plurality of parameters of the first patient at least partially matches the pattern of the second plurality of parameters of the second patient based on one or more machine learning models comprises:

determining that all of the first plurality of parameters match the second plurality of parameters.

6. The method of claim 1, wherein the one or more patient education instructions that are associated with the second patient are identified as corresponding to at least one of the second plurality of parameters that at least partially match the first plurality of parameters.

7. The method of claim 1, wherein the one or more patient education instructions that are associated with the second patient are identified as corresponding to all of the second plurality of parameters that match the first plurality of parameters.

8. The method of claim 1, wherein the first plurality of parameters includes two or more of age, gender, language, and race.

9. The method of claim 1, wherein the first plurality of parameters includes two or more of a chief complaint, a reason for a patient encounter, a presenting problem, a preliminary diagnosis, or a final diagnosis.

10. The method of claim 1, wherein the first plurality of parameters includes two or more a medical history, a clinician specialty, a surgical history, an education instruction, and a medication history.

11. One or more non-transitory computer-readable storage media having instructions embodied thereon, the instructions being executable by one or more processors to perform a method comprising:

generating a knowledge base for training one or more machine learning models, at least one of the one or more machine learning models comprising a clustering model, the knowledge base comprising parameters of prior patients and user selections of education instructions for the prior patients, the parameters including age, gender, language, race, a chief complaint, a reason for a patient encounter, a presenting problem, a preliminary diagnosis, a final diagnosis, a medical history, a clinician specialty, a surgical history, an education instruction, or a medication history;

generating the one or more machine learning models comprising the clustering model from the knowledge base;

receiving an indication to provide one or more recommendations for a first patient;

identifying a first plurality of parameters for the first patient, the first plurality of parameters includes two or more of age, gender, language, race, a chief complaint, a reason for a patient encounter, a presenting problem, a preliminary diagnosis, a final diagnosis, a medical history, a clinician specialty, a surgical history, an education instruction, or a medication history;

determining that a pattern of the first plurality of parameters of the first patient at least partially matches a pattern of a second plurality of parameters of a plurality of patients using one or more machine learning models, wherein determining that the pattern of the first plurality of parameters at least partially matches the pattern of the second plurality of parameters comprises: applying the one or more machine learning models to the parameters of the first patient;

in response to determining that the pattern of the first plurality of parameters at least partially matches the second plurality of parameters of the plurality of patients, calculating a score for each of the plurality of patients that at least partially match the first plurality of parameters of the first patient;

retrieving one or more patient education instructions that are associated with the plurality of patients that at least partially match the first plurality of parameters of the first patient; and communicating, to a clinician, the one or more patient education instructions as the one or more recommendations, wherein the one or more patient education instructions are communicated for display ranked by the score that corresponds to each of the plurality of patients that at least partially match the first plurality of parameters of the first patient;

responsive to determining that the clinician selected a particular patient education instruction, from the one or more patient education instructions, for the first patient, updating the knowledge base for retraining the one or more machine learning models based on the first plurality of parameters of the first patient and the particular patient education instruction.

12. The media of claim 11, wherein the one or more patient education instructions retrieved correspond to at least one of the partially-matching second plurality of parameters.

13. The media of claim 11, wherein the one or more patient education instructions are specific to one or more of the second plurality of parameters of the plurality of patients determined to at least partially match the first plurality of parameters, and wherein the second plurality of parameters include one or more of: a chief complaint, a reason for a patient encounter, a presenting problem, a preliminary diagnosis, or a final diagnosis.

14. The media of claim 11, wherein the one or more patient education instructions are specific to one or more of the second plurality of parameters of the plurality of patients determine to at least partially match the first plurality of parameters, and wherein the second plurality of parameters include two or more of a chief complaint, a reason for a patient encounter, a presenting problem, a preliminary diagnosis, or a final diagnosis.

15. The media of claim 11, wherein the score represents a strength of the at least partially matching of the pattern of the first plurality of parameters of the first patient to the second plurality of parameters of the plurality of patients.

16. The media of claim 11, further comprising ranking the plurality of patients that at least partially match the first plurality of parameters of the first patient based on the score for each of the plurality of patients.

17. The media of claim 11, further comprising:
receiving a selection of at least one of the one or more patient education instructions that were communicated;
in response to receiving the selection, associating the at least one of the one or more patient education instructions that was selected with the first plurality of parameters and with the first patient; and
storing the at least one of the one or more patient education instructions that was selected in association with the first plurality of parameters and in association with the first patient, wherein the first plurality of parameters of the first patient are used to subsequently determine pattern matching for a subsequent patient and the at least one of the one or more patient education instructions is subsequently used for a recommendation for the subsequent patient.

18. The media of claim 11, further comprising:
receiving a selection of a user-provided patient education instruction;
in response to receiving the selection, associating the user-provided patient education instruction that was selected with the first plurality of parameters and with the first patient; and
storing the user-provided patient education instruction that was selected in association with the first plurality of parameters and in association with the first patient, wherein the first plurality of parameters of the first patient are used to subsequently determine pattern matching for a subsequent patient and the user-provided patient education instruction is subsequently used for a recommendation for the subsequent patient.

19. A system for providing smart patient education recommendations via artificial intelligence and machine learning, the system comprising:
a memory storing instructions; and
one or more processors coupled to the memory, wherein the system is configured to execute the instructions using the one or more processors to perform operations comprising:
generating a knowledge base for training the one or more machine learning models, at least one of the one or more machine learning models comprising a clustering model, the knowledge base comprising parameters of prior patients and user selections of education instructions for the prior patients, the parameters including age, gender, language, race, a chief complaint, a reason for a patient encounter, a presenting problem, a preliminary diagnosis, a final diagnosis, a medical history, a clinician specialty, a surgical history, an education instruction, or a medication history;
generating the one or more machine learning models comprising the clustering model from the knowledge base;
receiving an indication to provide one or more recommendations for a first patient;
identifying a first plurality of parameters for the first patient, the first plurality of parameters includes two or more of age, gender, language, race, a chief complaint, a reason for a patient encounter, a presenting problem, a preliminary diagnosis, a final diagnosis, a medical history, a clinician specialty, a surgical history, an education instruction, or a medication history; and
determining that a pattern of the first plurality of parameters of the first patient at least partially matches a pattern of a second plurality of parameters of a plurality of patients using one or more machine learning models, wherein determining that the pattern of the first plurality of parameters at least partially matches the pattern of the second plurality of parameters of the plurality of patients comprises:
applying the one or more machine learning models to the parameters of the first patient;
in response to determining that the pattern of the first plurality of parameters at least partially matches the second plurality of parameters of the plurality of patients, calculating a score for each of the plurality of patients that at least partially match the first plurality of parameters of the first patient; and
retrieving one or more patient education instructions that are associated with each of the plurality of patients that at least partially match the first plurality of parameters of the first patient using one or more machine learning models; and communicating, to a clinician, the one or more patient education instructions as the one or more recommendations, wherein the one or more patient education instructions are communicated for display ranked by the score that corresponds to each of the plurality of patients that at least partially match the first plurality of parameters of the first patient; and responsive to determining that the clinician selected a particular patient education instruction, from the one or more patient education instructions, for the first patient, updating the knowledge base for retraining the one or more machine learning models based on the first plurality of parameters of the first patient and the particular patient education instruction.

20. The method of claim 1, further including using the first plurality of parameters of the first patient and the particular patient education instructions to determine pattern matching for a subsequent patient.

* * * * *